United States Patent
Matsumura et al.

(10) Patent No.: US 8,747,323 B2
(45) Date of Patent: Jun. 10, 2014

(54) PRESSING DEVICE, AND ULTRASONIC PROBE AND ULTRASONIC DIAGNOSTIC APPARATUS USING THE PRESSING DEVICE

(75) Inventors: Takeshi Matsumura, Tokyo (JP); Tsuyoshi Mitake, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 628 days.

(21) Appl. No.: 12/375,224

(22) PCT Filed: Jul. 31, 2007

(86) PCT No.: PCT/JP2007/064929
§ 371 (c)(1),
(2), (4) Date: Nov. 25, 2009

(87) PCT Pub. No.: WO2008/016022
PCT Pub. Date: Feb. 7, 2008

(65) Prior Publication Data
US 2010/0113937 A1  May 6, 2010

(30) Foreign Application Priority Data
Jul. 31, 2006   (JP) .................................. 2006-207455

(51) Int. Cl.
*A61B 8/14*   (2006.01)
(52) U.S. Cl.
USPC ............ 600/462; 600/437; 600/447; 600/459
(58) Field of Classification Search
None
See application file for complete search history.

(56) References Cited

U.S. PATENT DOCUMENTS

| 4,228,831 | A | * | 10/1980 | Kerns ......................... 73/864.12 |
| 5,190,046 | A | * | 3/1993 | Shturman ..................... 600/463 |
| 5,471,988 | A | | 12/1995 | Fujio et al. |
| 5,623,940 | A | * | 4/1997 | Daikuzono ................... 600/439 |

(Continued)

FOREIGN PATENT DOCUMENTS

| EP | 1 629 777 A1 | 3/2006 |
| JP | 06-169922 | 6/1994 |

(Continued)

OTHER PUBLICATIONS

Supplemental European Search Report, dated Nov. 10, 2010, issued in corresponding European Patent Application No. 07 79 1614.

(Continued)

*Primary Examiner* — Long V. Le
*Assistant Examiner* — Bo J Peng
(74) *Attorney, Agent, or Firm* — Antonelli, Terry, Stout & Kraus, LLP.

(57) ABSTRACT

A pressing device for smoothly performing pressing operation, an ultrasonic probe, and an ultrasonic diagnostic apparatus are provided.

The pressing device has a balloon installed on an ultrasonic transmission/reception surface of an ultrasonic probe and presses an object to be examined by the balloon.

The balloon has a hollow pressing unit made of an elastic material, a tube for charging/discharging liquid to/from the pressing unit, and an attachment part contiguous to the peripheral edge of the pressing unit and attaching the pressing unit to the ultrasonic transmission/reception unit of the ultrasonic probe.

The inner diameter of the attachment part or the pressing unit is set smaller than the outer diameter of the part of the ultrasonic probe on which the attachment part is attached.

Because tension is applied to the pressing unit, pressing operation can be started with a less amount of initial injection, and this makes the pressing operation smooth.

7 Claims, 15 Drawing Sheets

(56) References Cited

U.S. PATENT DOCUMENTS

| | | | |
|---|---|---|---|
| 5,779,731 A * | 7/1998 | Leavitt | 606/194 |
| 6,126,607 A * | 10/2000 | Whitmore et al. | 600/459 |
| 7,914,456 B2 * | 3/2011 | Osaka et al. | 600/447 |
| 2002/0068870 A1 | 6/2002 | Alam et al. | |
| 2004/0049111 A1 | 3/2004 | Hirooka et al. | |

FOREIGN PATENT DOCUMENTS

| | | |
|---|---|---|
| JP | 07-231894 | 9/1995 |
| JP | 09-140708 | 6/1997 |
| JP | 10-258058 | 9/1998 |
| JP | 2004-290414 | 10/2004 |
| JP | 2005-270236 | 10/2005 |
| JP | 2006-102240 | 4/2006 |
| JP | 2006-102240 A | 4/2006 |
| WO | WO 2006/041050 A1 | 4/2006 |

OTHER PUBLICATIONS

Chinese Office Action dated Jun. 24, 2010, issued in corresponding Chinese Patent Application No. 200780027653.7.

JP Office Action for Japanese Application No. 2008-527747, issued on Dec. 19, 2012.

* cited by examiner

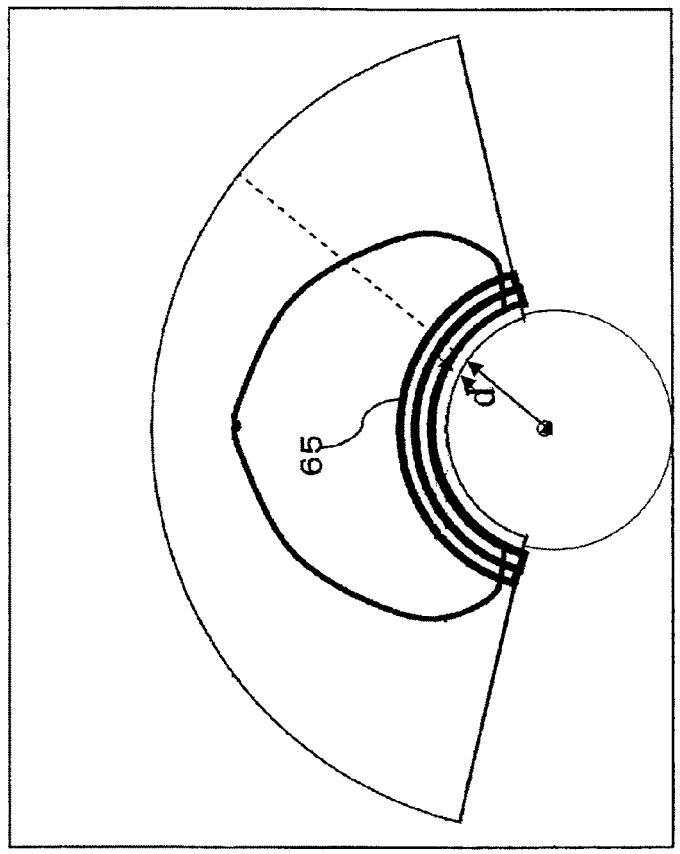
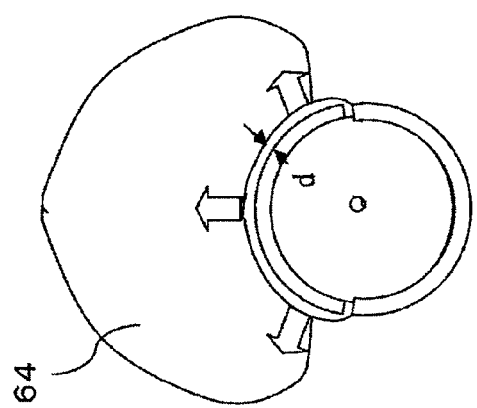
FIG.7

FIG.8
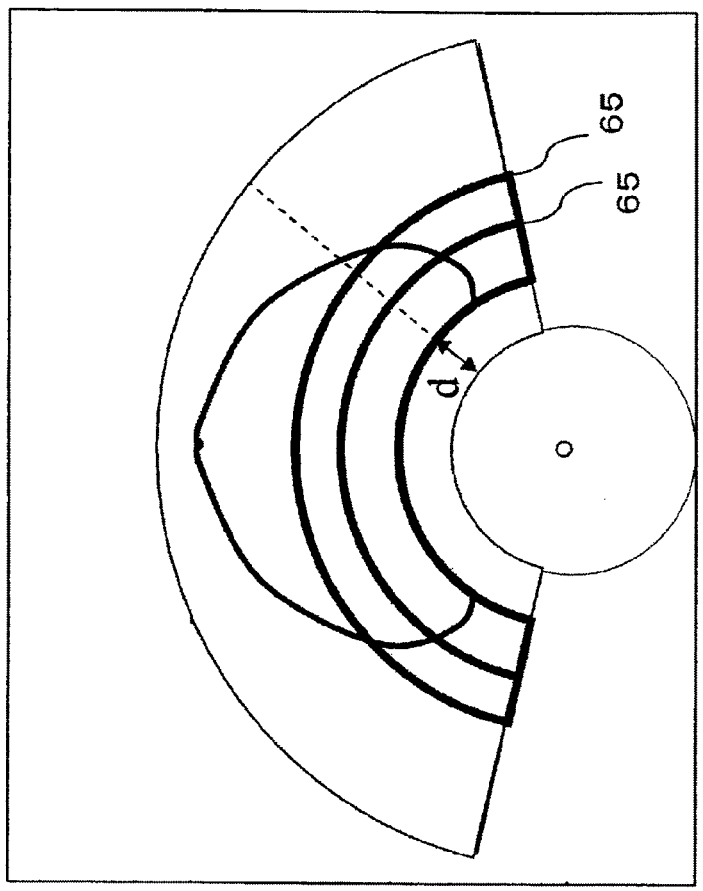
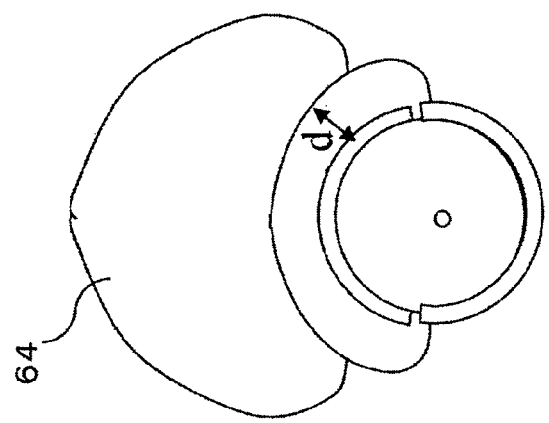

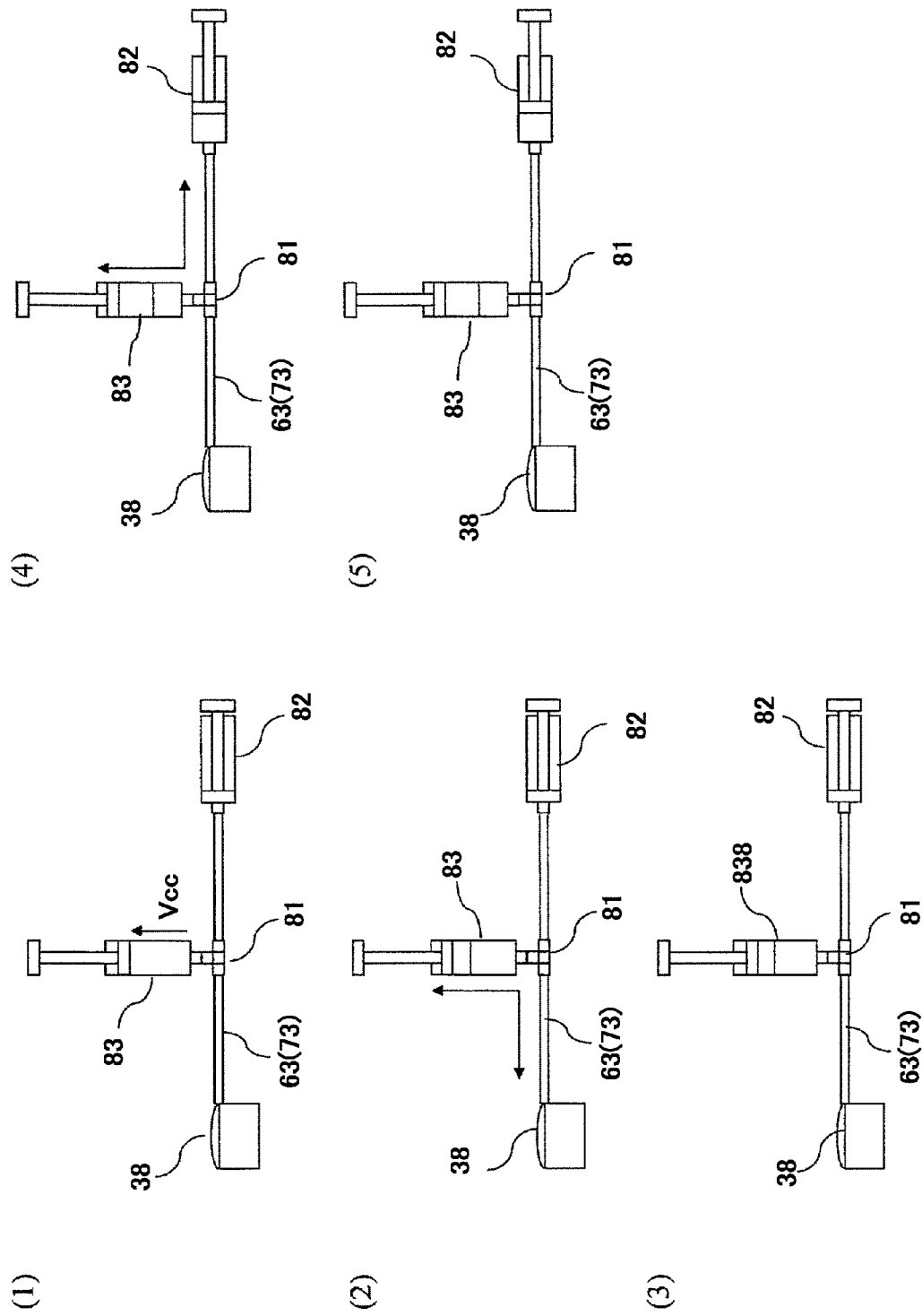

PRESSING DEVICE, AND ULTRASONIC PROBE AND ULTRASONIC DIAGNOSTIC APPARATUS USING THE PRESSING DEVICE

TECHNICAL FIELD

The present invention relates to a pressing device, and an ultrasonic probe and ultrasonic diagnostic apparatus using the same to be used for acquiring elasticity information in ultrasound diagnostics.

BACKGROUND ART

In ultrasound diagnostics, presence of tumors or presence of malignant tumors such as a cancer is diagnosed by measuring the hardness or softness of tissues in an object to be examined. In concrete terms, pressure is applied to biological tissues, displacement in each area of the object caused by the pressure is measured, elasticity information such as strain or elasticity modulus of each area is calculated based on the measured displacement, and the calculated elasticity information is imaged to be provided for diagnosis.

As a method for adding pressure to the object, it is common to apply an ultrasonic transmission/reception surface of an ultrasonic probe to the target tissues in the object manually or mechanically. Instead of pressing an ultrasonic probe manually on the skin surface of an object, a pressing device of a transrectal ultrasonic probe to be used by inserting into a body cavity for diagnosis of a prostate gland, etc. is proposed in Patent Document 1 and Patent Document 2.
Patent Document 1: US Patent No. 2002/0068870A1
Patent Document 2: WO2006/041050A1

DISCLOSURE OF THE INVENTION

Problems to be Solved

However, in accordance with the pressing method disclosed in the Patent Document 1 and Patent Document 2, in the case of inserting into a body cavity having diameter larger than the diameter of the ultrasonic probe head, the space between the surface of the ultrasonic probe and the membrane need to be filled with substantial amount of liquid in order to acquire enough pressure.

Therefore, since charging of the large quantity of liquid is required initially to reach the threshold value of the tension generated on the balloon membrane, time delay will be caused until necessary pressure is generated for measurement. In other words, due to large quantity of liquid required for initial filling, smooth pressing operation of repeating addition of minute pressing by charging and discharging of liquid and may be hindered.

The objective of the present invention is to provide a pressing device for performing smooth pressing operation, an ultrasonic probe and ultrasonic diagnostic apparatus using the pressing device thereof.

Means to Solve the Problem

In order to solve the above-described problem, in the pressing device of the present invention comprising a balloon to be attached to the ultrasonic transmission/reception surface of the ultrasonic probe and for pressing an object using the balloon thereof, the balloon is provided with a pressing unit which is hollow and is formed by an elastic member, a tube for charging/discharging liquid to/from the pressing unit, an attaching unit coupled to the peripheral border of the pressing unit and for attaching the pressing unit to the ultrasonic transmission/reception surface of the ultrasonic probe, and the internal diameter of the attaching unit or the pressing unit is configured smaller than the external diameter of the part to which the pressing unit is to be attached in the ultrasonic probe. Since the tensile force is applied to the pressing unit, the pressing operation can be started smoothly with a small amount of liquid for initial filling, which leads to a smooth pressing operation.

Also, in the ultrasonic probe comprising an end part having an ultrasonic transmission/reception surface, a grip coupled to the end part to be grasped and held by an examiner and a pressing device for pressing an object by a balloon, the balloon has a pressing unit which is hollow and is formed by an elastic member, a tube for charging/discharging liquid to/from the pressing unit and an attaching unit for attaching the pressing unit to an ultrasonic transmission/reception surface, and the pressing unit is attached to the ultrasonic transmission/reception surface in a state to which the tensile force is being applied. Since tensile force is applied to the pressing unit, the pressing operation can be started smoothly with a small amount of liquid for initial injection which leads to a smooth pressing operation.

Also, the ultrasonic probe is provided to the ultrasonic diagnostic apparatus for transmitting ultrasonic waves from an ultrasonic probe having a pressing device for applying pressure to biological tissues of an object to be examined, acquiring elasticity information of the biological tissues in the plurality of measuring points based on a pair of the frame data which is obtained by measuring reflected echo signals generated from the object, constructing and displaying elastic images based on the acquired elasticity information. Since tensile force is applied to the pressing unit, pressing operation can be started smoothly with a small amount of liquid for initial injection which leads to a smooth pressing operation. Further, since the thickness of the liquid layer in the pressing unit can be made thinner, it is possible to obtain the elastic images wherein the influence from the noise generated due to multiple reflections in the liquid layer is being suppressed.

BRIEF DESCRIPTION OF THE DIAGRAMS

Figure 6:
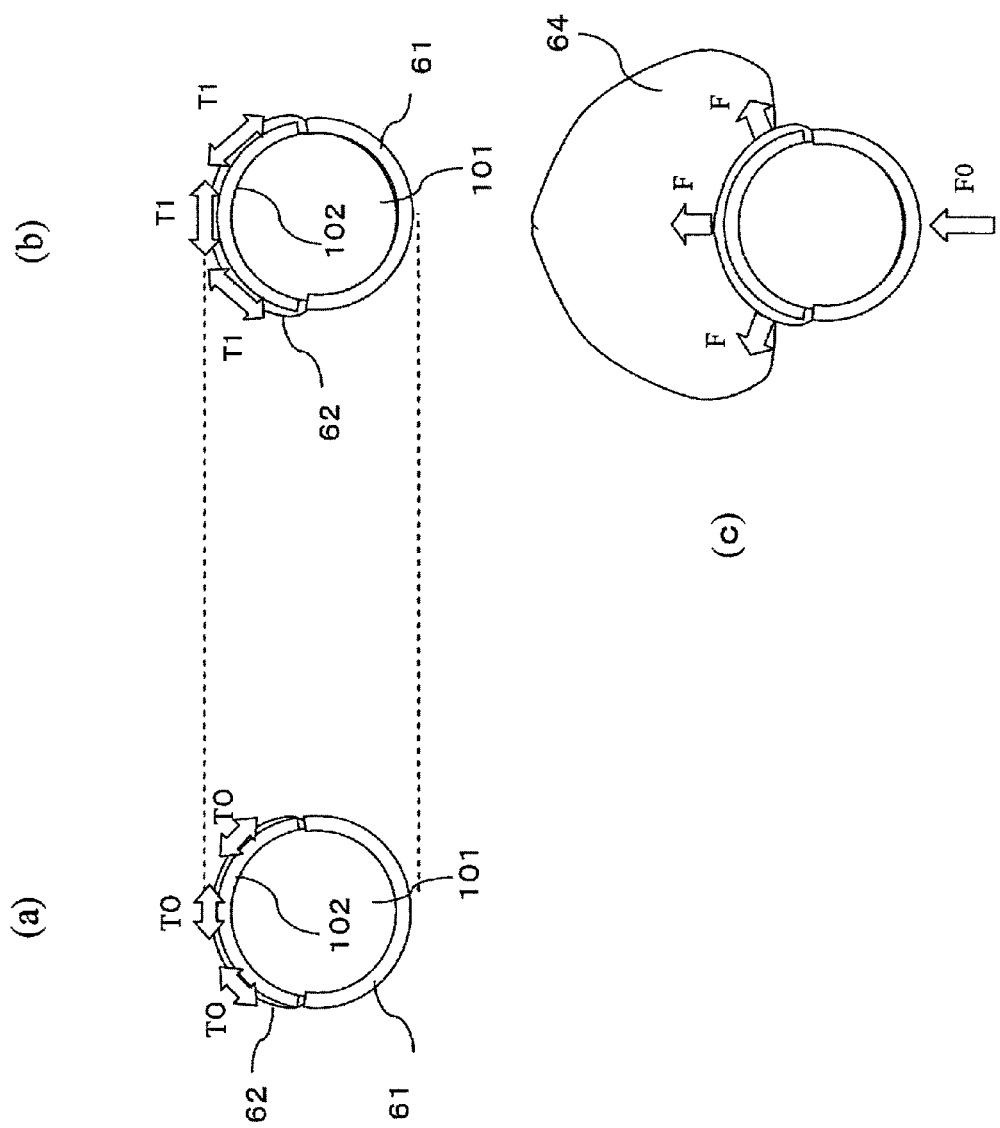

FIG. 6 explains the pressing operation of the balloon to which the initial tension is added in the embodiment 1.

FIG. 7 explains the noise of multiple reflections generated due to a liquid layer in a balloon.

FIG. 8 explains the noise generated due to multiple reflections in the case that the liquid layer is thick.

Figure 9:
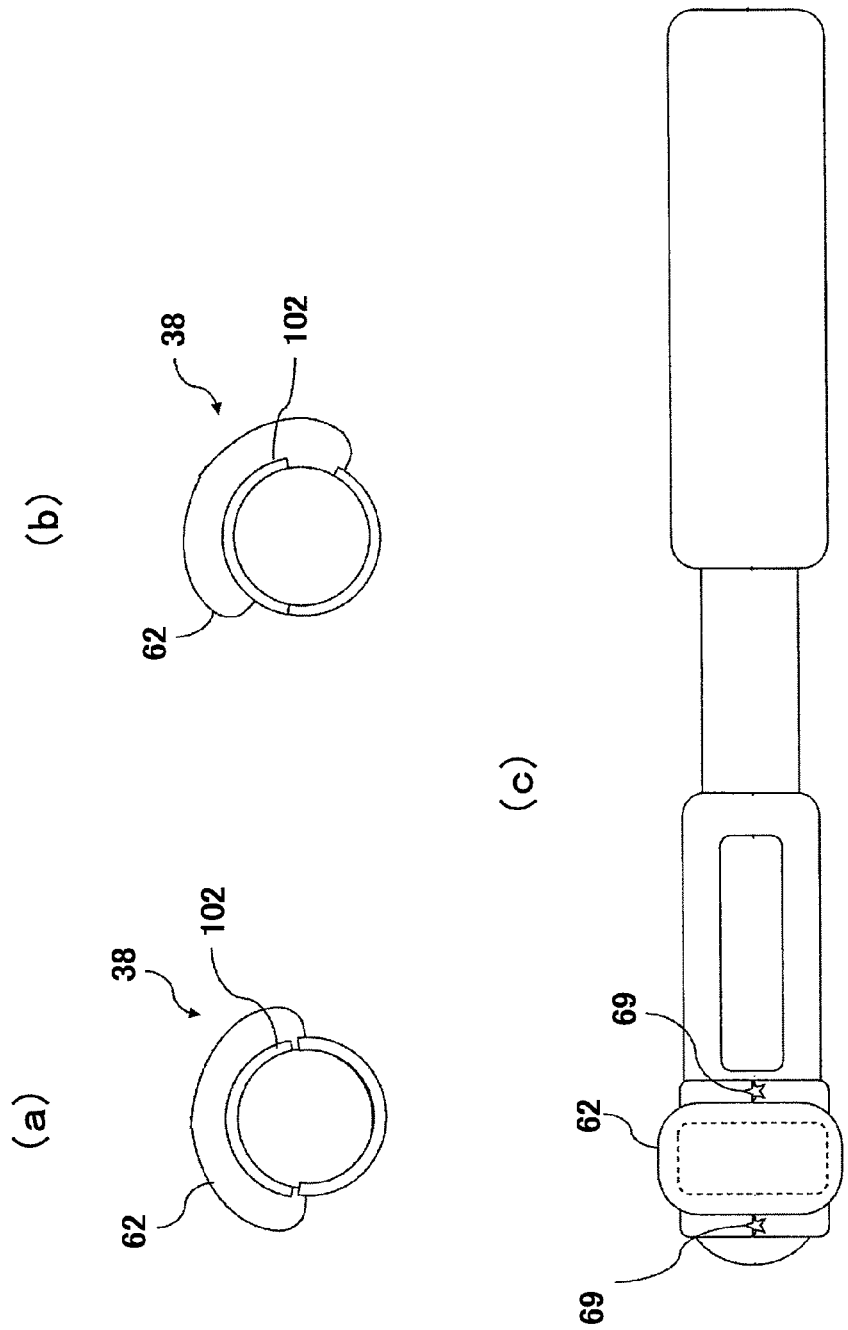

FIG. 9 shows a practical example of appending marks for attaching a balloon in an adequate position.

Figure 10:
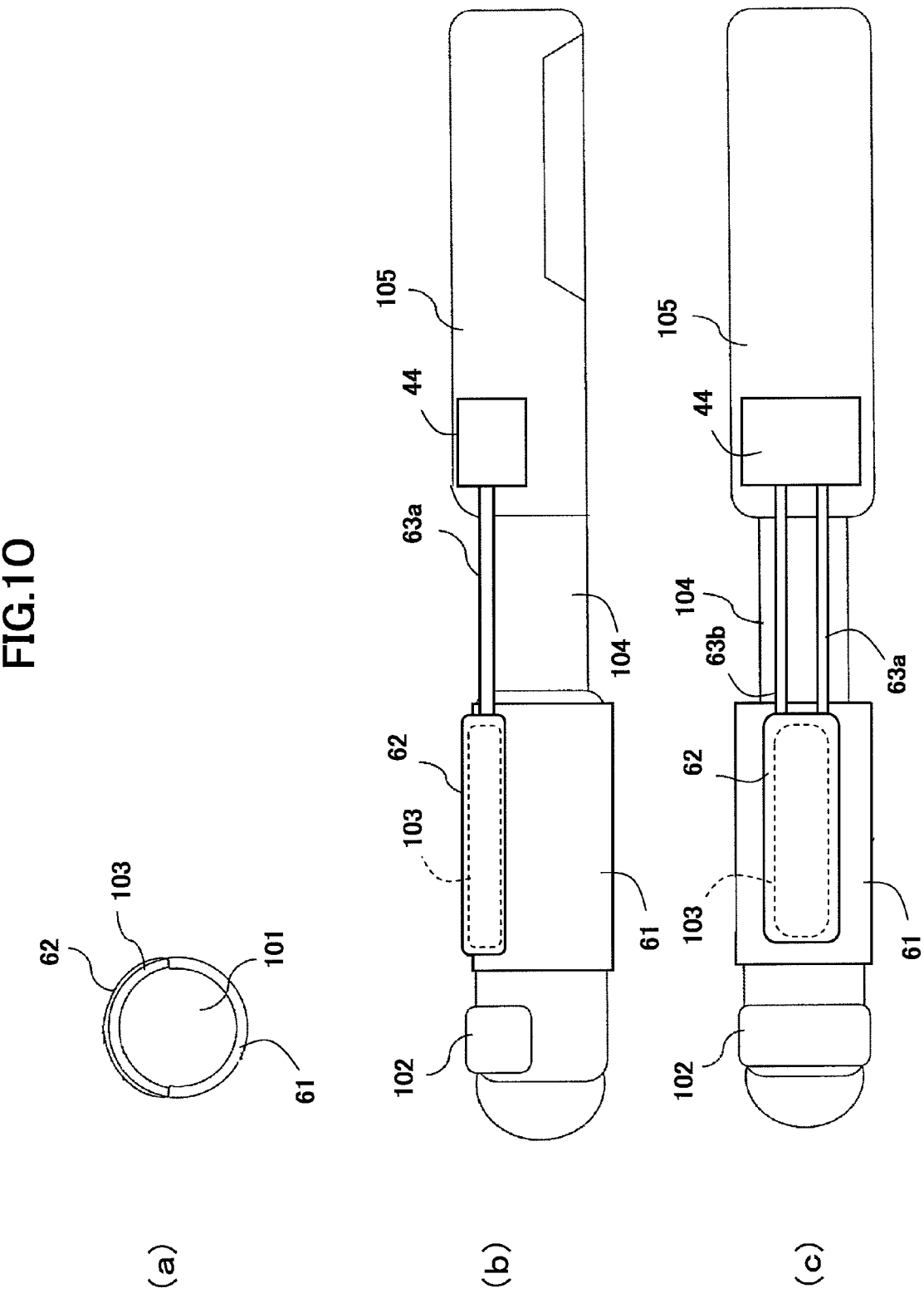

FIG. 10 is a configuration diagram of an ultrasonic probe to which the balloon in embodiment 2 is attached.

Figure 11:
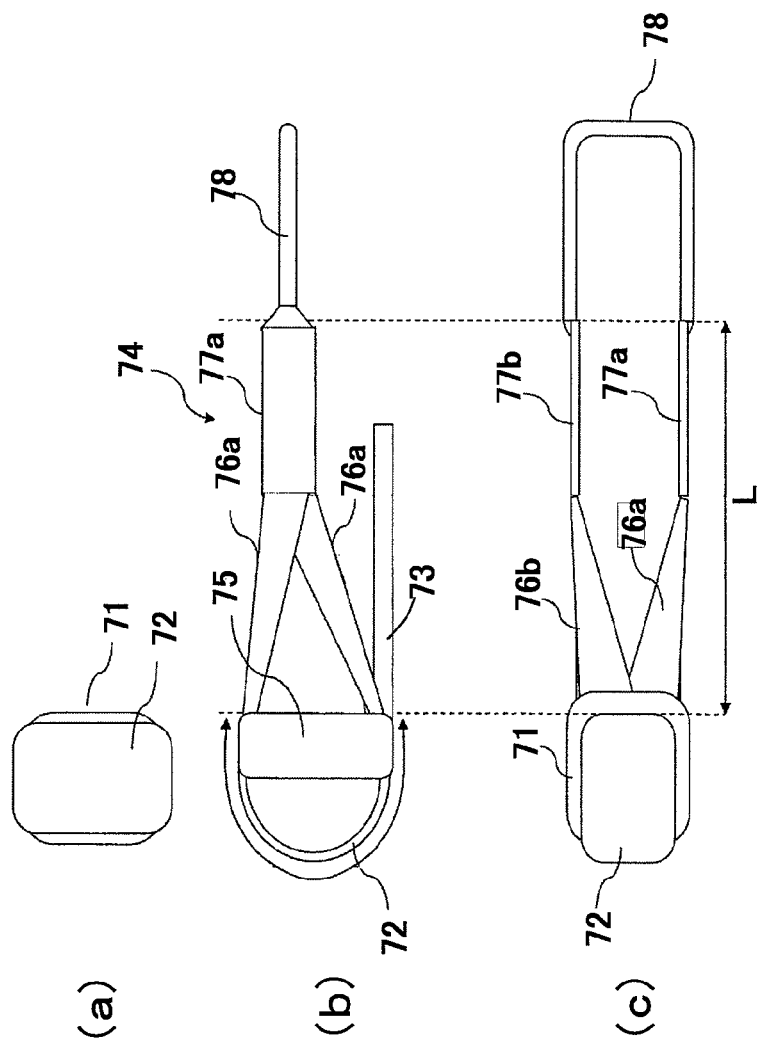

FIG. 11 is a configuration diagram of embodiment 3 related to a balloon of the pressing device in the present invention.

Figure 12:
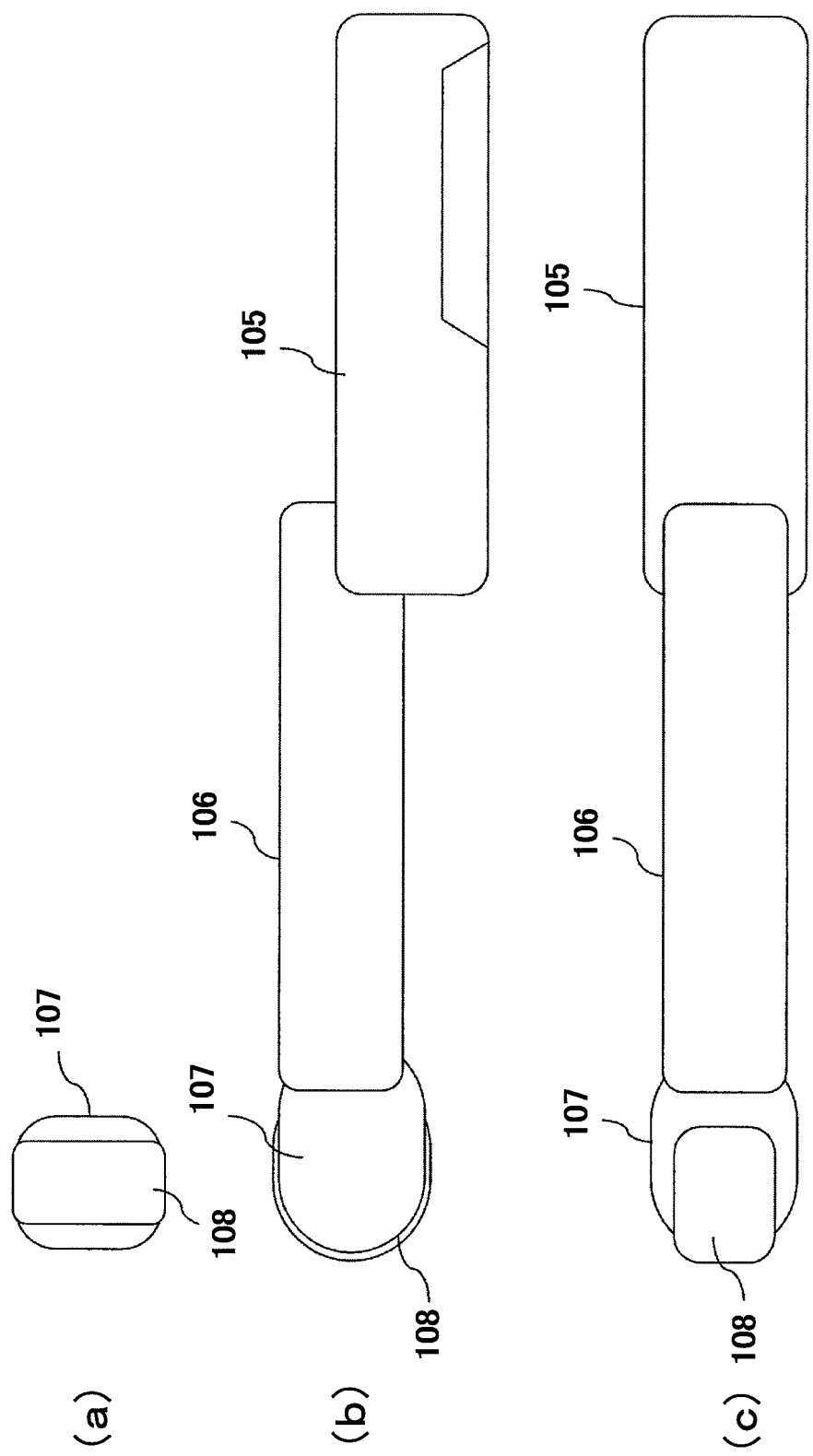

FIG. 12 is a configuration diagram of an example of the end-fire type ultrasonic probe to which the balloon in embodiment 3 is attached.

Figure 13:
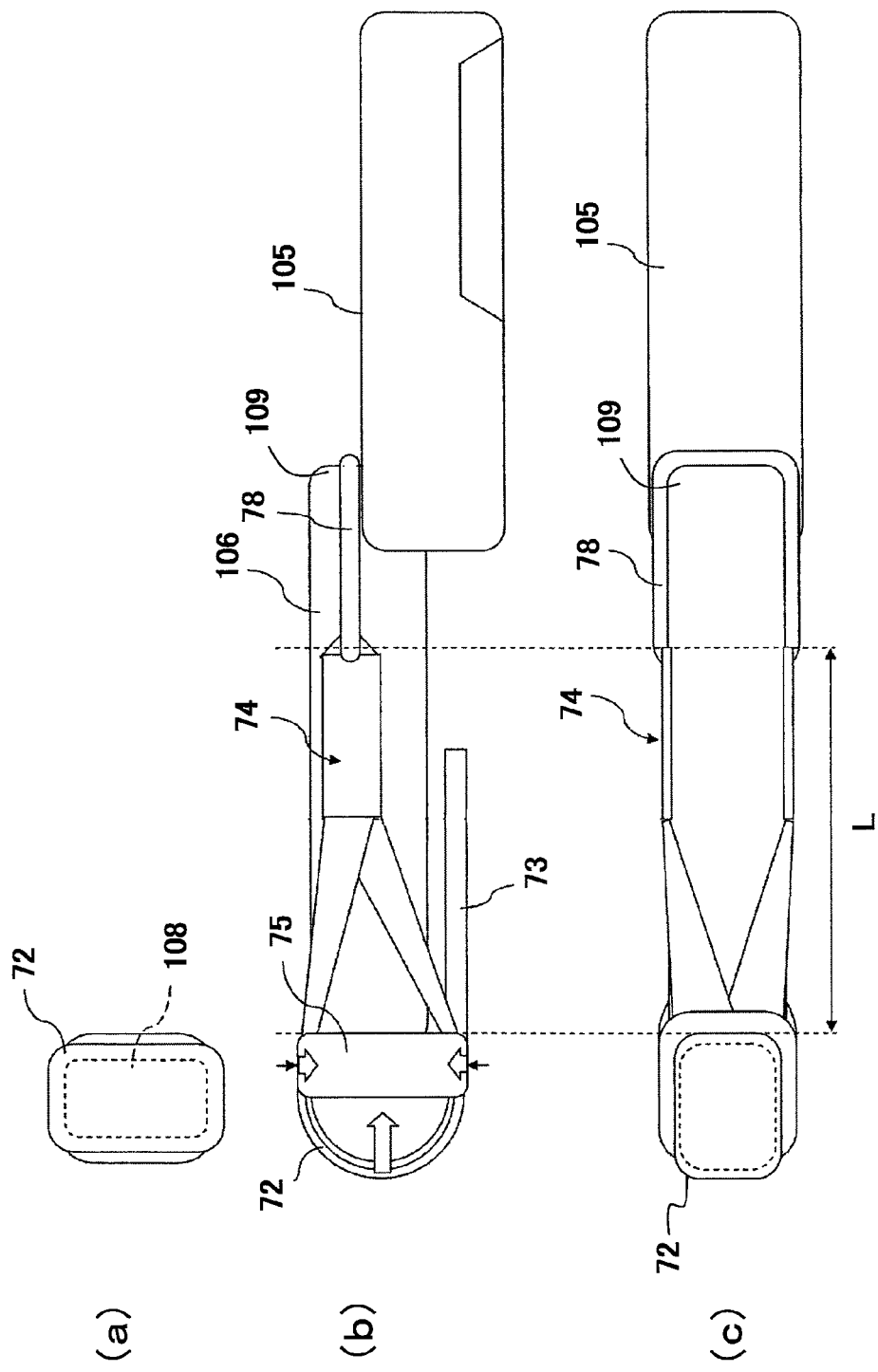

FIG. 13 shows the condition wherein the balloon in the embodiment 3 is attached to an end-fire type ultrasonic probe.

Figure 14:
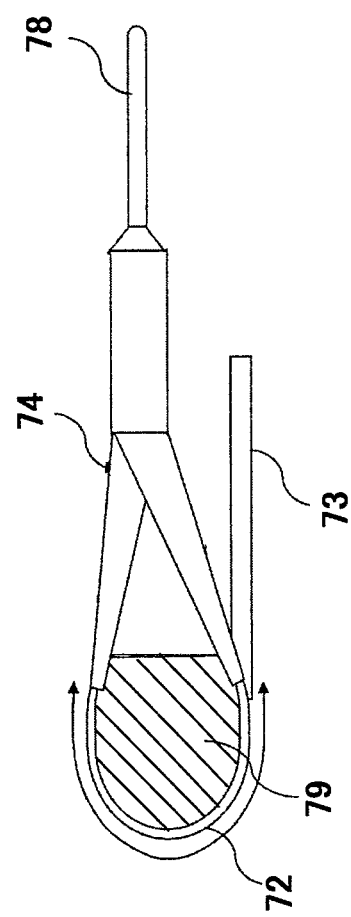

FIG. 14 is a configuration diagram of variation example of the balloon in the embodiment 3.

FIG. 15 is a configuration diagram of a practical example of a pressing operation unit for charging/discharging liquid to/from a balloon.

BEST MODE FOR CARRYING OUT THE INVENTION

Figure 1:
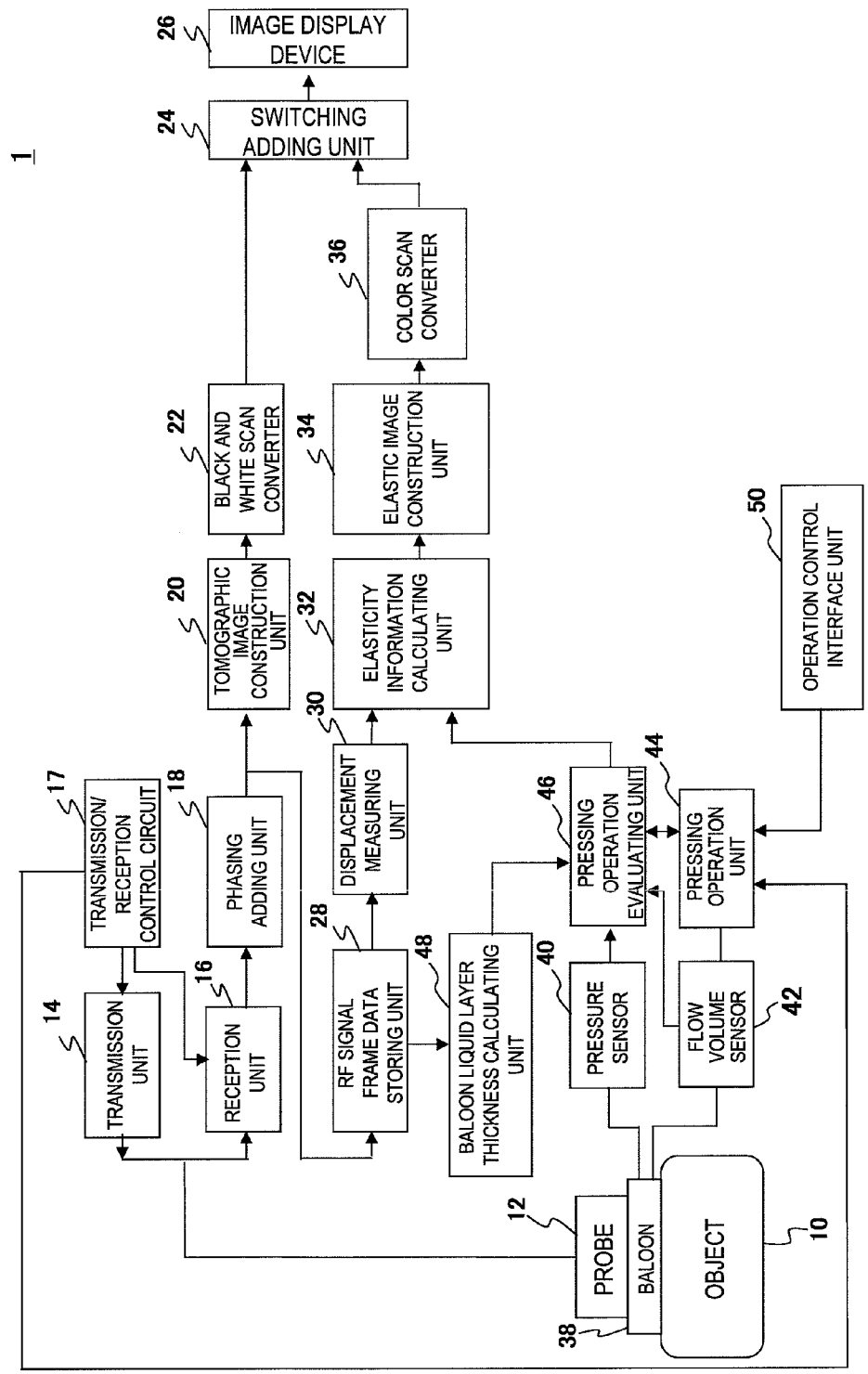
FIG. 1 is a block diagram showing the configuration of the ultrasonic diagnostic apparatus to which the pressing device related to the present invention is applied.

Hereinafter, embodiments of a pressing device, and ultrasonic probe and ultrasonic diagnostic apparatus using the pressing device to which the present invention is applied will be described referring to the diagrams. FIG. 1 is a block diagram showing the configuration of an embodiment of the ultrasonic diagnostic apparatus to which the pressing device related to the present invention is applied.

As shown in FIG. 1, an ultrasonic diagnostic apparatus 1 comprises:

an ultrasonic probe 12 for applying to an object 10 via a balloon 38;

a transmission unit 14 for repeatedly transmitting ultrasonic waves to the object 10 via the ultrasonic probe 12 at specified time intervals;

a reception unit 16 for receiving the reflected echo signals in time series generated from the object 10;

a transmission/reception control unit 17 for controlling the transmission unit 14 and the reception unit 16; and a phasing and adding unit 18 for phasing and adding the reflected echoes received in the reception unit 16. The RF signal frame data outputted from the phasing and adding unit 18 is transmitted to a tomographic image construction unit 20 where grayscale tomographic images (for example, black and white B-mode images) of the object are to be constructed. The output signals of the grayscale tomographic image constructed by the tomographic image construction unit 20 are converted in the black and white scan converter 22 so as to be corresponded to the display on an image display device 26.

Also, the RF signal frame data outputted from the phasing and adding unit 18 is stored in an RF signal frame data storing unit 28. A displacement measuring unit 30 selects at least two sets of frame data from the RF signal frame data storing unit 28, and measures the displacement of the biological tissues of the object 10. The displacement information measured in the displacement measuring unit 30 is inputted to an elasticity information calculating unit 32 and strain or elasticity modulus of the biological tissues is obtained therein. The strain or elasticity modulus calculated in the elasticity information calculating unit 32 is inputted to an elastic image constructing unit 34 for constructing color elastic images corresponding to the calculated strain or the elasticity modulus. The output signals of the color elastic image constructed in the elastic image constructing unit 34 is inputted to a color scan converter 36 and the signals are converted therein so as to be corresponded to the display of the image display device 26. A switching/adding unit 24 switches the display patterns for superimposing or juxtaposing the B-mode image outputted from the black and white scan converter 22 and the color elastic image outputted from the color scan converter 36, and displays the synthesized image to the image display device 26. The detailed explanation on the above-described configuration of an ultrasonic diagnostic apparatus will be omitted since it is of the commonly known ultrasonic diagnostic apparatus.

Next, characterized configuration of the pressing device and the ultrasonic probe using the pressing device thereof related to the present invention will be described in detail. The pressing device of the present embodiment is configured comprising a balloon 38, a pressure sensor 40, a flow sensor 42, a pressing operation unit 44, a pressing operation evaluating unit 46 and a balloon liquid layer calculating unit 48. The balloon 38 for pressing the object 10 is attached to the ultrasonic probe 12. The balloon 38 formed in a saclike shape by a material capable of being passed through by ultrasonic waves, and is adhered on to the ultrasonic transmission/reception surface of the ultrasonic probe 12. It is preferable that the balloon 38 has a membrane made of a material safe for a living body such as polyurethane, vinyl chloride, latex (natural rubber) or silicon, and also formed by a material having elasticity.

The inside of the balloon 38 is filled with liquid such as water or oil, and is expanded/deflated by charging/discharging the liquid to/from the balloon 38 by the pressing operation unit 44. When the balloon 38 is expanded by the pressure operation unit 44 the pressure to the object 10 can be increased, and when the balloon 38 is deflated the pressure to the object 10 can be reduced. The operation of the pressing operation unit 44 is automatically carried out in a device control interface unit 50, but can also be carried out manually.

Also, charging/discharging flow volume of the liquid to be charged/discharged by the pressure operation unit 44 is detected by the flow sensor 42. The pressure of the liquid inside of the balloon 38 is detected by the pressure sensor 40. The balloon liquid layer thickness calculating unit 48 calculates the thickness of the liquid layer in the ultrasonic waves transmitting direction of the balloon 38 based on the RF signal frame data in the RF signal frame data storing unit 28, and obtains the charging/discharging flow volume of the liquid being charged/discharged to/from the balloon 38. The pressing operation evaluating unit 46 calculates the pressure to be added (compression) to the tissues in the ultrasonic scanning region of the object 10 to which the balloon 38 is applied from the charging/discharging flow volume of the liquid obtained by the flow sensor 42 or the balloon liquid thickness calculating unit 48 or the pressure of the liquid detected by the pressure sensor 40. The pressure information calculated in the pressing operation evaluating unit 46 is inputted to the elasticity information calculating unit 32, and the elasticity modulus is obtained from the displacement information in the displacement measuring unit 30.

Hereinafter, the present invention will be described based on embodiments of the pressing device.

Embodiment 1

Figure 2:
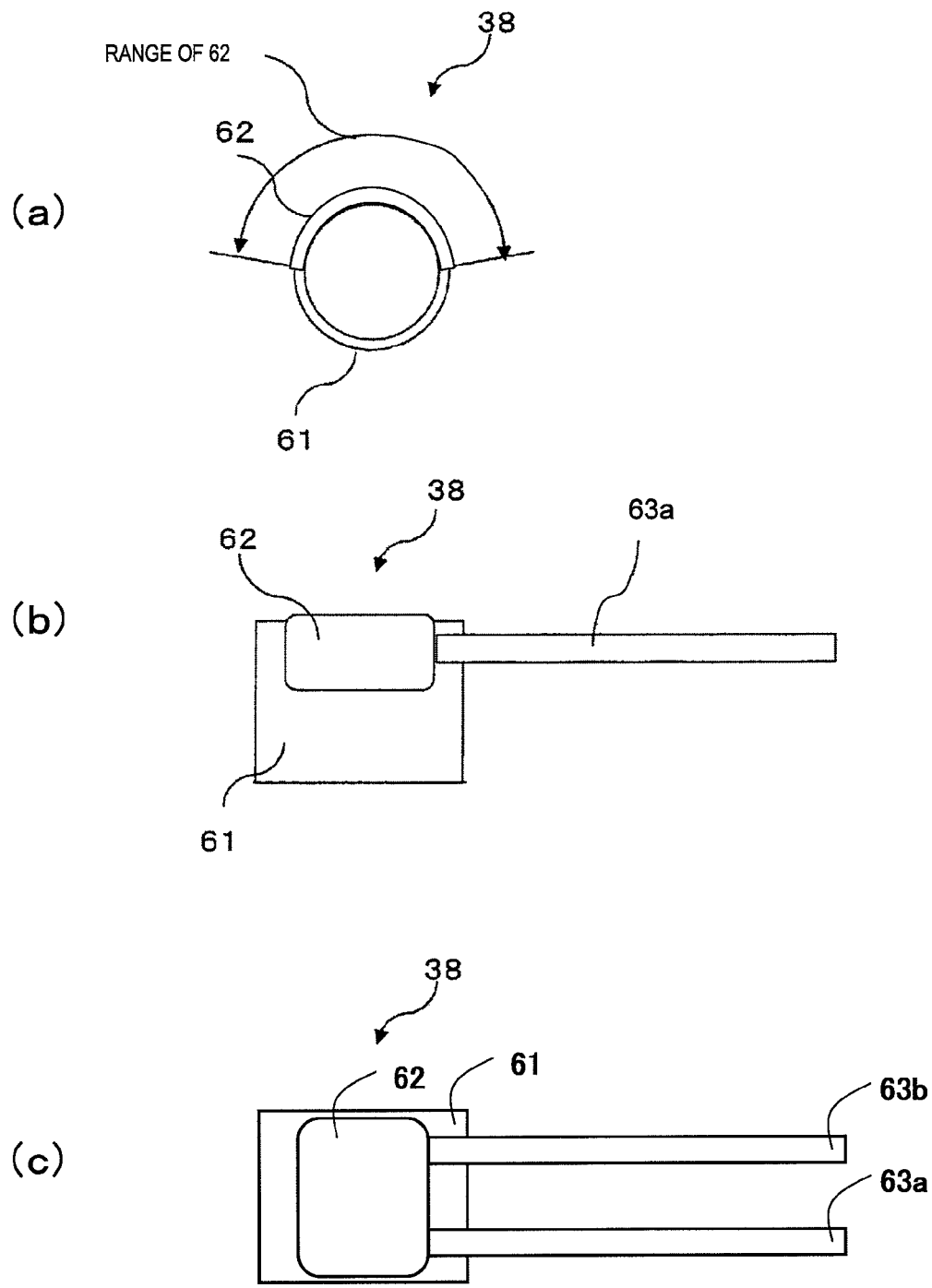
FIG. 2 is a configuration diagram of embodiment 1 of a balloon related to the pressing device of the present invention.
Figure 3:
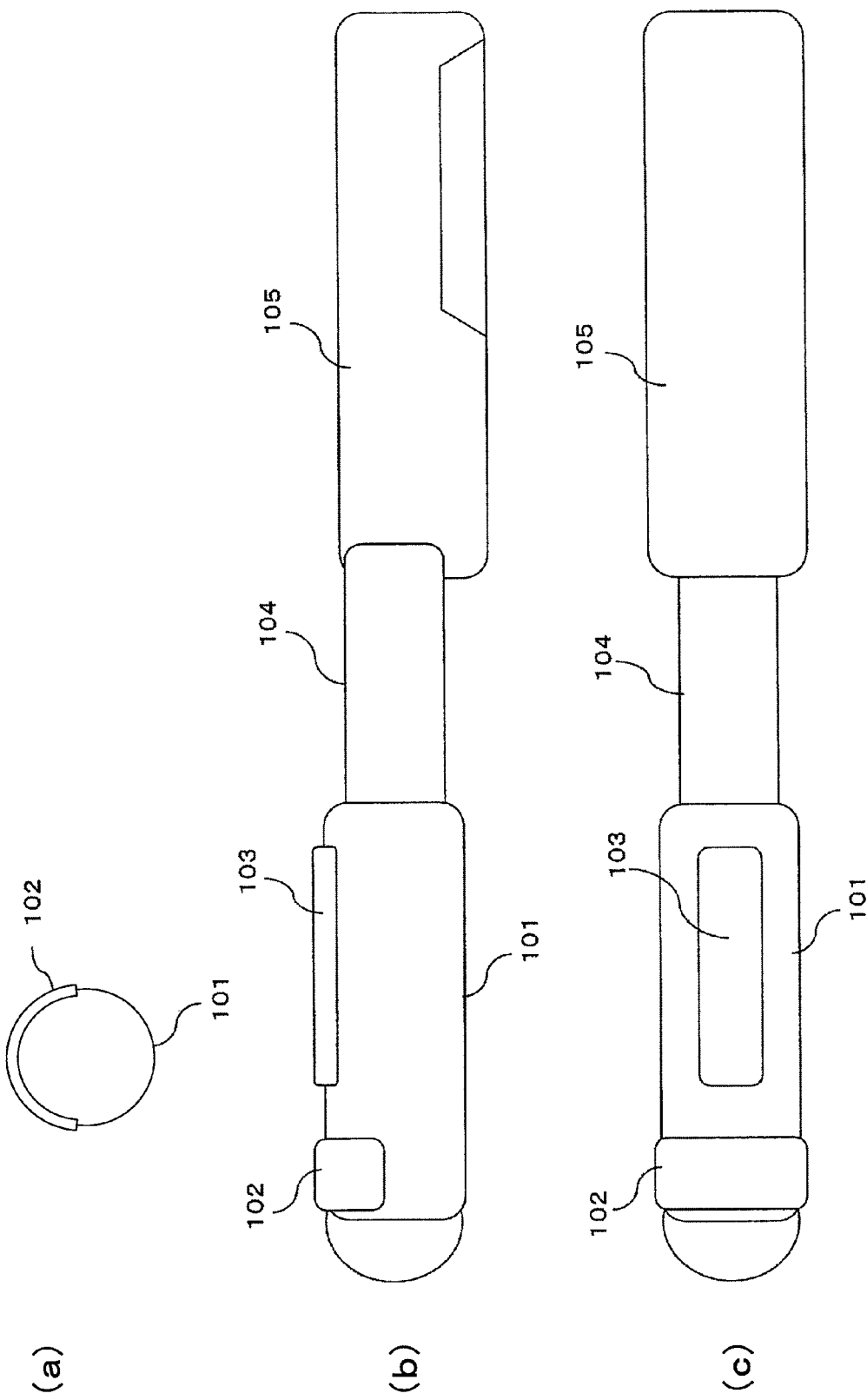
FIG. 3 is a configuration diagram showing an example of the ultrasonic probe to which a balloon described in the embodiment 1 is to be attached.
Figure 4:
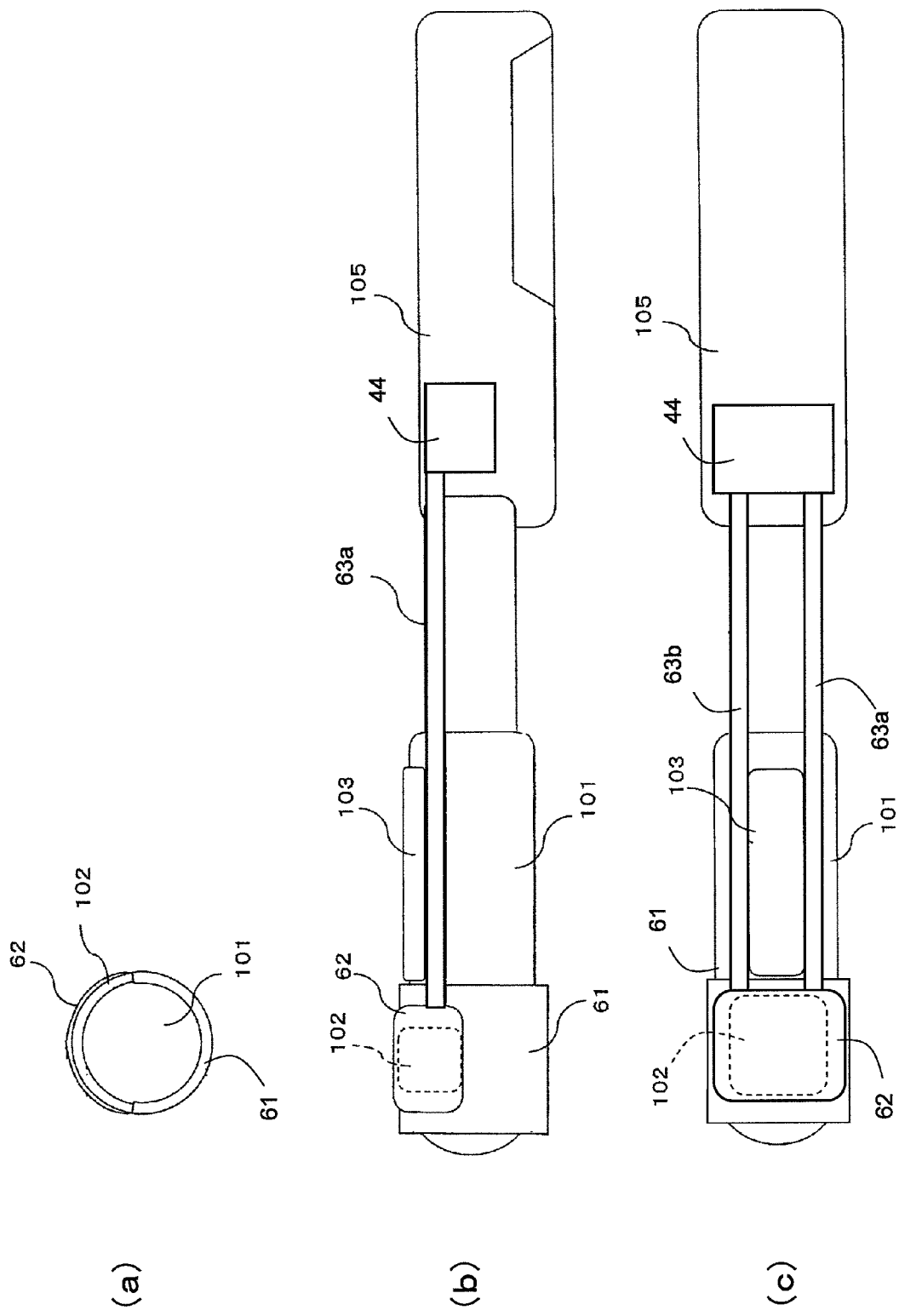
FIG. 4 is a configuration diagram of the ultrasonic probe to which the balloon in the embodiment 1 is attached.

FIG. 2 is a configuration diagram of the embodiment 1 of the balloon 38 related to the pressing device of the present invention, FIG. 3 is a configuration diagram showing an example of the ultrasonic probe 12, and FIG. 4 is a configuration diagram showing an example of the ultrasonic probe 12 to which the balloon 38 is attached.

FIG. 2(a) is a diagram of the balloon 38 being viewed from the end side, FIG. 2(b) is a side view and FIG. 2(c) is a top view. As shown in FIG. 2(a), the balloon 38 is formed in a cylinder (ring) shape by a band-like sheet member 61 having elasticity. The internal diameter of the cylindrical attachment part 61 of the band-like sheet member is formed smaller than the external diameter of an ultrasonic probe head 101 (the part to which the attachment part is attached) of the ultrasonic probe 12. Then as shown in FIG. 2(*b*)(*c*), the hallow pressing unit 62 is formed in a part of the band-like sheet member 61, communicated with the pressing unit 62, and provided with tubes 63*a* and 63*b* for charging/discharging liquid to/from the pressing unit 62. In other words, the attachment part 61 is juncturally connected to the periphery of the pressing unit 62. The pressing unit 62 is formed having a larger area than the area of the ultrasonic transmission/reception surface 102. The other end of the tubes 63*a* and 63*b* is to be coupled to the pressing operation unit 44 in FIG. 1.

The ultrasonic probe 12 shown in FIG. 3 is referred to as a transrectal ultrasonic probe. It has a cylindrical ultrasonic probe head 101 to be inserted in a body cavity, and an ultrasonic transmission/reception surface 102 having a group of transducers for a horizontal section and an ultrasonic transmission/reception surface 103 having a group of transducers for the longitudinal section which is orthogonal to the horizontal section are provided on the outer surface of the ultrasonic probe head 101. The ultrasonic probe head 101 is coupled to a grip 105 for grabbing and holding with a hand of an examiner via a cylindrical coupling part 104. FIG. 3(*a*) shows the ultrasonic probe head 101 being viewed from the end-side, FIG. 3(*b*) is the side view and FIG. 3(*c*) is the top view.

FIG. 4 shows the form of the ultrasonic probe 12 after attaching the balloon 38. FIG. 4(*a*) shows the ultrasonic probe head 101 being viewed from the end-side, FIG. 4(*b*) is the side view and FIG. 4(*c*) is the top view. The attachment part 61 has a cylinder shape, and is spread and wound on the periphery of the ultrasonic probe head 101 of the ultrasonic probe 12. The attachment part 61 is for attaching the pressing unit 62 to the ultrasonic transmission/reception surface 102, and is attached to the ultrasonic transmission/reception surface 102 in the condition that the tensile force is applied. In this manner, cylindrical shaped band-like sheet member 61 is formed also as the attachment part 61 for attaching the balloon 38 to the ultrasonic probe 12.

Figure 5:
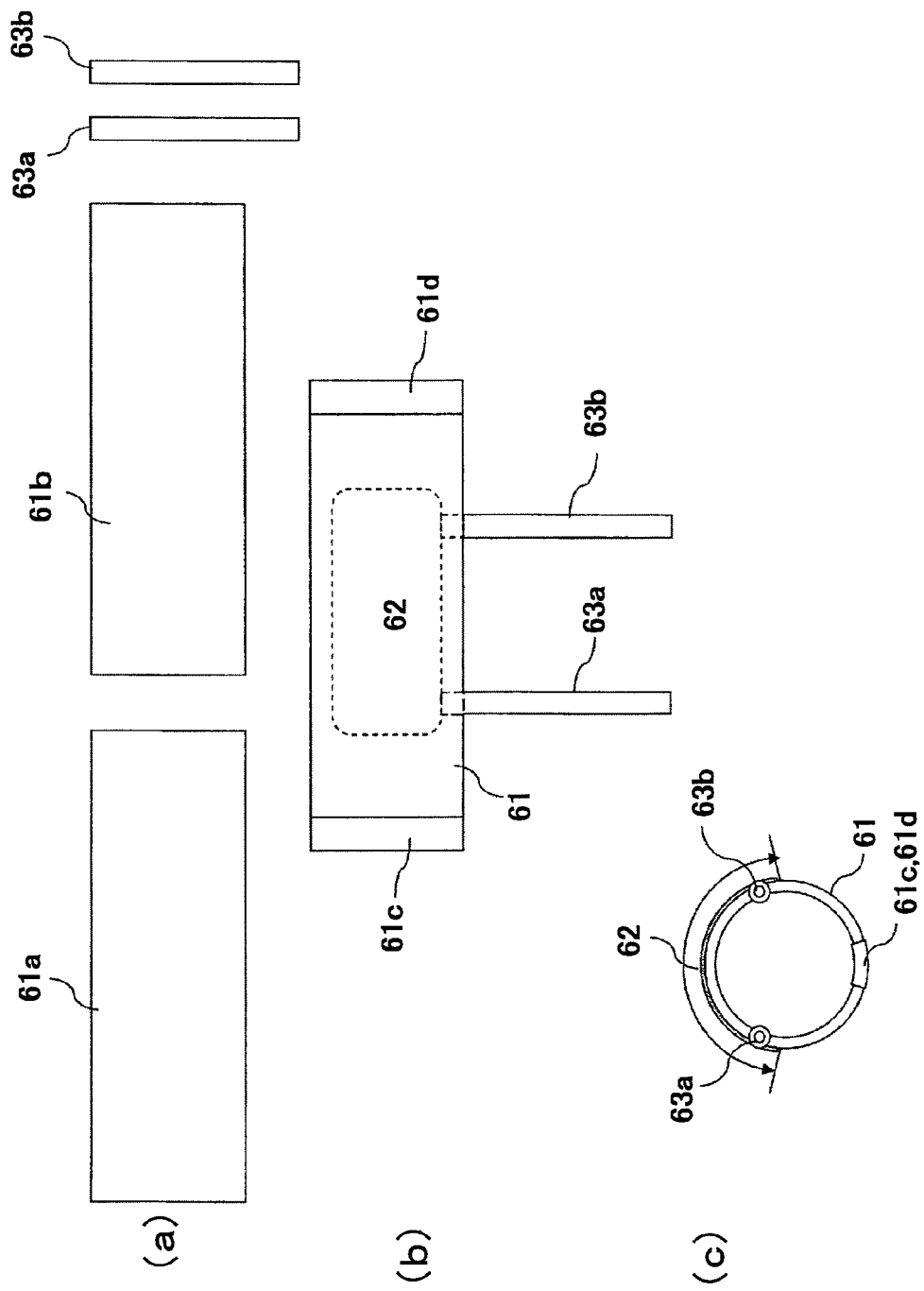
FIG. 5 shows the method for manufacturing the balloon in the embodiment 1.

The manufacturing method of the balloon 38 in the embodiment 1 will be described referring to FIG. 5. As shown in FIG. 5(*a*), the balloon 38 is formed by two pieces of band-like sheet members 61*a* and 61*b* having the same shape and elasticity, and two tubes 63*a* and 63*b*. As shown in FIG. 5(*b*), the end of the two tubes 63*a* and 63*b* are positioned in the region where the pressing unit 62 is formed, and the periphery part of the two pieces of band-like sheet members 61*a* and 61*b* is welded and sealed closely excluding the region in which the pressing unit 62 is formed. At this time, the outer surface of the band-like sheet members 61*a* and 61*b* and the tubes 63*a* and 63*b* are also adhered to each other. Accordingly, the pressing unit 62 can be formed in a part of the band-like sheet member 61. Then as shown in FIG. 5(*c*), the cylindrical balloon 38 can be formed by overlapping and welding both of the end-parts 61*c* and 61*d* of the band-like sheet member 61. The sealing method of the band-like sheets 61*a* and 61*b* and the tubes 63*a* and 63*b* does not have to be limited to welding, and may be adhered using a powerful adhesive to seal up the pressing unit 62. The welding or adhering needs to be carried out so that the flow channel of the two tubes 63*a* and 63*b* will not be blocked off. Also, the tubes 63*a* and 63*b* are to be connected to the pressing operation unit 44 being merely juxtaposed.

In this way, the reason for juxtaposing two tubes is to make the tubes 63*a* and 63*b* easy to insert into a body cavity by forming the diameter of them small and the outward form of the ultrasonic probe 12 small including the ultrasonic probe head. Also, in the case that air bubbles get into the liquid in the pressing unit 62, the air bubbles are to be removed by charging liquid to the pressing unit 62 from the tube 63*a* and discharging the liquid from the pressing unit 62 to the tube 63*b*.

Such balloon 38 in the present embodiment has the cylindrical shaped attachment part formed by the elastic band-like sheet member 61 and the internal diameter of the attachment part is formed smaller than the external diameter of the ultrasonic probe head 101 (the part where the pressing unit is attached) of the ultrasonic probe 12, thus when it is attached to the ultrasonic probe head 101, the attachment part of the band-like sheet member 61 is spread and attached. Then the balloon 38 is attached by aggressively constricting the ultrasonic probe head 101 using the tensile force added upon deflation of the attachment part, and the tensile force (initial tension) is applied to the sheet membrane of the pressing unit 62. This initial tension can be adjusted by changing the cylindrical diameter of the band-like sheet member 61. For example, when the cylindrical diameter of the band-like sheet member 61 is enlarged the initial tension decreases, and when the cylindrical diameter of the band-like sheet member 61 is made smaller the initial tension increases.

Also, it can be adjusted by elasticity or thickness of the band-like sheet member 61. For example, when the material of the band-like sheet member 61 is made thin the initial tension decreases, and when the material of the band-like sheet member is made thick the initial tension increases.

The material to be used for the band-like sheet member 61 is elasticated material such as silicon system, urethane system, vinyl (chloroethene) system or latex (natural rubber) system. The band-like sheet member 61 should be configured by the material, which when stretched, does not get damaged and returns quickly to the original condition. In particular, it is preferable to use the material formed in accurately even thickness.

While the pressing unit 62 is formed by superimposing two pieces of band-like sheets 61 in the present embodiment, the pressing unit 62 may be attached to the ultrasonic transmission/reception surface by forming a hallow pressing unit 62 from one member, adhering a strip band to both ends of the pressing unit 62 thereof and winding the band on the ultrasonic probe head 101 (the part to which the pressing unit is attached).

The such operation for adding pressure to the object 10 by charging/discharging liquid using the pressing operation unit 44 to/from the balloon 38 while the tensile force is being applied will be described referring to FIG. 6. FIG. 6(*a*) shows the condition of the balloon 38 right after being attached to the ultrasonic probe 12, and FIG. 6(*b*) shows the condition when the charging of liquid to the balloon attached to the ultrasonic probe 12 has started. As shown in FIG. 6(*a*), initial tension T0 is added to the sheet membrane of the pressing unit 62 by attaching the balloon 38 to the ultrasonic probe 12. Therefore, when the liquid is charged to the inside of the balloon 38, the pressure of the liquid in the pressing unit 62 is the initial pressure P0 corresponding to the initial tension T0.

Further, when liquid is charged to the pressing unit 62 and the pressure surpasses the threshold tension T1 corresponding to the counterbalancing pressure to the pressing pressure F0 of the ultrasonic probe 12, the expansion of the pressing unit 62 starts as shown in FIG. 6(*b*). In this manner, the pressure F to be added to target tissues 64 of the object 10 is increased, and strain is generated in the target tissues 64.

Therefore, in accordance with the pressing device and ultrasonic probe in the present embodiment, the pressing operation by the balloon 38 can be started promptly with less initial charging volume V0. Especially, in the entire region of the sheet membrane surface of the pressing unit 62, the pressing unit 62 can be expanded or deflated sensitively even with minimum variation of charging volume ΔV (for example, about 0.1~0.5 cc), and strain can be generated in the target tissues 64 with a delicate pressing operation. Also, since the threshold tension T1 is given over to the entire region of the sheet membrane surface, even when there is a surface region not in contact with the target tissues, the pressure which is counterbalancing to the threshold tension can be added to the region surface contacted with the biological tissues, without concentration of expansion/deflation on the region where there is no contact with the tissues. Such advantage enables smooth pressing operation.

Also, in accordance with the present embodiment, since the initial charging volume V0 of liquid to the balloon 38 can be made less, the thickness "d" of the liquid layer in the pressing unit 62 can be made thin. As a result, it is possible to acquire elastic images wherein influence of noise generated due to multiple reflections in the liquid layer is suppressed. In particular, in the balloon 38 of the present embodiment 1, if the initial tension T0 is set at a value more than threshold tension T1, the target tissues 64 can be pressed by an imperceptible charging volume variation ΔV even in the condition that the initial charging volume V0 is almost zero.

Therefore, as shown in FIG. 7, the range that the noise 65 of multiple reflections is generated can be suppressed down to the range close to the ultrasonic transmission/reception surface of the ultrasonic probe 12. Ultrasonic waves excite intense reflex upon transmission in the border of the region where there is difference in acoustic impedance, in accordance with the degree of the difference. Therefore, reflex is excited in the border between the sheet surface of the pressing unit 62 and the skin surface of the target tissues 64, the reflected ultrasonic waves are further reflected in the ultrasonic transmission/reception surface 102, and transmitted again in the direction of the target tissues 64. Multiple occurrence of such phenomenon takes place in the liquid layer of the pressing unit 62, and the noise 65 of multiple reflections appears in the places which are integral multiplication distance of the distance "d" between the ultrasonic transmission/reception surface 102 and the sheet membrane surface of the pressing unit 62 (=skin surface of the target tissues 64), as shown in the diagram on the right side of FIG. 7. Since this noise is overlapped with the target tissues 64 (for example, a prostate gland region), the elasticity information to be calculated based on the RF reception signals overlapped with the noise is also influenced by the noise, which lowers the accuracy of diagnosis.

In accordance with the conventional technique which does not apply initial tension to a balloon requires much of the initial charging volume V0' to charge into the balloon for generating the threshold tension T1, whereby making the thickness "d'" of the liquid layer of the balloon 38 to be thick as shown in the comparative example of FIG. 8. Therefore, the noise 65 of multiple reflections in the liquid layer appears in the wide range of elastic images and deteriorates S/N of the images. The technique referred to as TGC (Time Gain control) or STC (Sensitivity Time Control) has been commonly applied to the ultrasonic diagnostic apparatuses that construct B-mode images by amplifying the reflected echo signals on a greater scale when the depth of derivation of the signals is deeper. However, the farther the position is where reflection occurs on the sheet membrane surface of the balloon 38 from the ultrasonic transmission/reception surface 102 of the ultrasonic probe 12 the greater the noise caused by the reflection increases in intensity, whereby drastically deteriorating S/N of the elastic images.

While the balloon 38 to use for a transrectal ultrasonic probe is exemplified in the present embodiment 1, the present embodiment does not have to be limited to the particular probe thereof, and may be used for the ultrasonic probe wherein the ultrasonic transmission/reception surface is extended to the periphery surface of the tubelike ultrasonic probe head in the circumferential direction. Such ultrasonic probe is known to be used, other than the transrectal ultrasonic probe, as a transesophageal ultrasonic probe, transvaginal ultrasonic probe, fingertip-worn ultrasonic probe, microprobe for a blood vessel and endoscopic probe.

Though it is preferable that the initial tension T0 of the pressing unit 62 surpasses the threshold tension T1 corresponding to the pressure counterbalancing to the pressure force F0 of the ultrasonic probe 12, it is not necessarily the case. If tensile force is added in advance to the pressing unit 62, the initial charging volume V0 until it surpasses the threshold tension T1 can be made less than the conventional method, which makes it possible to expedite the start of pressing operation and reduce image deterioration of elastic images due to noise of multiple reflections.

In accordance with the pressing device of the present embodiment 1, the balloon 38 attached to the ultrasonic transmission/reception surface of the ultrasonic probe 12 is pressed on target tissues, and the pressure force F at that time is stored as a reference pressing state. Then the state that the initial charging volume V0 is given to the balloon 38 is set as an initial state. By measuring the pressure "P" of the liquid in the balloon 38 by the pressure sensor 40 upon the initial state, the pressure force "F" per unit area can be calculated in the pressing operation evaluating unit 46. Thus the charging/discharging of the liquid in the balloon 38 is carried out by controlling the pressure controlling unit 44 so as to make the pressure force per unit to be the reference pressing state. After that, by charging/discharging liquid of minute charging volume variation ΔV regarding the reference pressing state as its origin, the pressing unit 62 of the balloon is expanded/deflated so as to give a minute pressing variation ΔP to the target tissues 64. By using the displacement variation of the tissues generated inside of the target tissues 64 due to the above-mentioned pressure variation ΔP, as commonly known, strain variation Δε and/or elasticity modulus of the tissues generated inside of the target tissue 64 is calculated in the elasticity information calculating unit 32 so as to obtain the elasticity information for diagnosis. For example, strain distribution is calculated as elasticity information, and strain images are further constructed as elastic images and displayed on the image display device 26. In accordance with the present embodiment, an examiner can perform elasticity diagnosis in real time.

Since the balloon 38 and the tube 63 are to be inserted into a body cavity of a living body along with the ultrasonic probe 12 and gets contaminated upon examination, they are to be disposed after each use in the same manner as, for example, ultrasonic probe covers used for the common ultrasound examination or surgery of prostate gland. Also, the balloon 38 and the tube 63 are sterilized (for example, γ sterilization), and packed in a bag, etc. to be stored.

Additionally, as shown in FIG. 9(b), when the central position of the balloon 38 is attached without matching the central position of the ultrasonic transmission/reception surface of the horizontal section, the uniformity of the pressure in the right and left direction is not secured. Given this factor, as shown in FIG. 9(c), it is preferable that a mark 69 indicating the central position of the balloon 38 is appended on the attachment part of the balloon 38. This mark may be indicated by printing, and by welding or adhering a protruded part on the balloon 38. In this manner, the balloon 38 can be easily and surely attached to a predetermined position by matching the mark of the balloon 38 to the central position of the ultrasonic transmission/reception surface of the cross section of the ultrasonic probe, whereby avoiding the inhomogeneous pressure due to the inappropriate attachment and improving the repeatability of diagnosis. Also, the position of the mark 69 does not have to be limited to the central position of the balloon 38, and may be appended to, for example, the part which is on the 180° opposite side thereof on the back surface of the ultrasonic probe for confirming a predetermined position with respect to the probe.

Embodiment 2

FIG. 10 is a configuration diagram showing an example of an ultrasonic probe 12 to which the balloon 38 of the present embodiment 2 is attached. The difference from the embodiment 1 is that a hollow pressing unit 62 is attached to the ultrasonic transmission/reception surface 103.

FIG. 10 shows a form of the ultrasonic probe 12 after the balloon 38 is attached to it. FIG. 10(a) is a diagram being viewed from the end-side of the ultrasonic probe head 101 to which the balloon 38 is attached. FIG. 10(b) is a side view and FIG. 10(c) is a top view. The attachment part 61 has a tubelike shape, and is spread and wound on the periphery of the ultrasonic probe head 101 of the ultrasonic probe 12. The attachment part 61 is juncturally connected to the periphery of the pressing unit 62. The attachment part 61 attaches the pressing unit 62 to the ultrasonic transmission/reception surface 103, and the pressing unit 62 is attached to the ultrasonic transmission/reception surface 103 in the condition that the tensile force is imparted. In this way, the band-like sheet member 61 formed in a cylinder shape is formed also as the attaching part 61 for attaching the balloon 38 to the ultrasonic probe 12. The ultrasonic transmission/reception surface 103 is linear, but the pressing unit 62 can be attached to the ultrasonic transmission/reception surface 103 by the attaching part 61.

In the embodiments 1 and 2, the case that one balloon 38 being attached to one ultrasonic probe 12 is exemplified. However, the present invention is not limited to those embodiments, and when two ultrasonic transmission/reception surfaces 102 and 103 are provided to one ultrasonic probe head of the ultrasonic probe 12, two balloons 38 can be independently attached to each of the ultrasonic transmission/reception surfaces 102 and 103. In this case, it is preferable to attach the two balloons 38 at the same time by coupling the two balloons 38 to form them in an integrated manner.

Also, it is preferable to couple the respective two balloons 38 independently and to control them respectively. It also is possible to couple both of the balloons 38 to the pressing operation unit 44 so as to operate them at the same time.

For example, upon examination, it is set so that the ultrasonic transmission/reception surface 103 of the longitudinal section is preferentially operated, and can be configured so that when switched to the longitudinal section the balloon 38 of the longitudinal section is automatically expanded/deflated and when switched to the horizontal section the balloon 38 of the horizontal section is automatically expanded/deflated.

Also, while both of the balloons 38 are independently expanded/deflated in the case of the real-time biplane setting, it is preferable to expand/deflate them alternately so that one of the cross-sections will not have displacement upon pressing.

In either case, pressing velocity (charging/discharging volume) is varied in conformity to the frame rate so the pressing operation can be performed in an adequate strain range by coordinating with the control signals of the ultrasonic diagnostic apparatus to control the pressing operation unit 44.

Embodiment 3

FIG. 11 is a configuration diagram showing an example of the embodiment 3 of the balloon 38 related to the pressing device of the present invention, and FIG. 12 is a configuration diagram showing an example of the ultrasonic probe 12 to which the balloon 38 of the present embodiment 3 is attached.

The ultrasonic probe 12 using the pressing device of the present embodiment 3 has an ultrasonic probe head 107 having a half-cylinder shaped end surface fixed to the end portion of the cylinder-shaped insertion unit 106, and is provided with an ultrasonic transmission/reception surface 108 having a transducer group on the cylindrical surface of the ultrasonic probe head 107 as shown in FIG. 12. Such ultrasonic probe 12 is generally used for the transrectal probe referred to as an end-fire type. FIG. 12(a) is a front view of the ultrasonic transmission/reception surface 108, (b) is the side view of the ultrasonic probe 12 and FIG. 12(c) is a top view of the ultrasonic probe 12.

FIG. 11 shows the balloon 38 to use for the end-fire type ultrasonic probe 12. In FIG. 11, (a) is a front view of the balloon 38 corresponding to the ultrasonic transmission/reception surface 108, (b) is a side view and (c) is a top view. As shown in these diagrams, the band-like sheet member 71 (attachment part) of the balloon 38 is coupled to the periphery of the pressing unit 72. It is provided with the tube 73 coupled to the pressing unit 72, and the attachment part 74 is connected to both ends of the band-like sheet member 71. The other end of the tube 73 is coupled to the pressing operation unit 44 shown in FIG. 1. The attachment part 74 is for applying tensile force to the sheet membrane of the pressing unit 72 of the band-like sheet member 71. Also, a pair of band-like members 75 (attachment part) formed by material having elasticity is coupled to the side border of both ends of the band-like sheet members 71. Since the internal diameter of the band-like member 75 is smaller than the external diameter of the ultrasonic probe head 107 of the ultrasonic probe head 107 (the part to which the pressing unit is attached) of the ultrasonic probe 12, the band-like sheet member 71 is constricted and attached to the ultrasonic transmission/reception surface 108 by the elasticity of the band-like member 75.

The attachment part 74 is configured having two pairs of bands 76a and 76B coupled to the both ends of band-like sheet member 71 respectively, coupling bands 77a and 77B for coupling the bands 76a and 76B of each pair and a hook band 78 for coupling the other end of the coupling bands 77a and 77B. At least a part of the respective bands which configure the attachment part 74 is formed by a material having elasticity. Such configured balloon 38 is for being attached to the end fire type of ultrasonic probe 12 as shown in FIG. 13. In FIG. 13, (a) is a front view of the balloon 38 being attached to the ultrasonic transmission/reception surface 108, (b) is a side view thereof and (c) is a top view. As shown in these diagrams, while a ring-shaped unit formed by a pair of band-like members 75 for coupling both ends of the band-like sheet members 71 is being spread, the pressing unit 72 is positioned to the ultrasonic transmission/reception surface 108 and attached to the ultrasonic probe head 107. Then the entire attachment part 74 is extended, and the hook band 78 is engaged to an engaging unit 109 in the posterior end of the inserting unit 106. In this manner, both ends of the band-like sheet member 71 are pulled, the sheet membrane of the pressing unit 72 is extended in the longitudinal direction, and initial tensile force is applied. Also, by the tensile force of a pair of the band-like members 75, both ends of the band-like sheet member 71 are expanded in the circumferential direction of the ultrasonic probe head 107, and the tensile force in the short-axis direction is added to the sheet membrane of the pressing unit 72 in compliance with the expansion. In this manner, the sheet membrane of the pressing unit 72 can be attached over the circumferential direction of the half-cylinder shaped ultrasonic probe head 108 with the same constriction force.

The initial tensile force "T0" of the sheet membrane of the pressing unit 72 can be adjusted by, for example, setting a length "L" of the bands 76a and 76B and the coupling bands 77a and 77B at a sufficiently shorter distance compared to the length of the inserting unit 106. The preferable material for the bands 76a and 76B and the coupling bands 77a and 77B is the one having elasticity which is comparatively hard and inextensible. Also, the material comparatively hard and inextensible such as urethane tube is preferable for the hook band 78. Also, the member for the above-mentioned band 76, coupling band 77 and hook band 78 does not have to be separate from the band-sheet member 71, and may be integrated with the band-like sheet member 71.

Also, by adjusting the length of the inserting unit 106 in the longitudinal direction, the constriction force of the pressing unit 72 can be arbitrarily adjusted. The inserting unit 106 has a configuration capable of expanding or contracting in the longitudinal direction by comprising therein a gear or wire, etc. (not shown in the diagram). Thus when the inserting unit 106 is expanded in the longitudinal direction the constriction force of the pressing unit 72 becomes large, and when the inserting unit 106 is contracted in the longitudinal direction the constriction force of the pressing unit 72 becomes small. Accordingly, by adjusting the length of the inserting unit 106 in the longitudinal direction, the constriction force of the pressing unit 72 can be optimally adjusted.

As shown in FIG. 13(b), the end region in the longitudinal direction of the sheet membrane of the pressing unit 72 and the central region thereof have different degrees of constricting pressure which is constricted toward the tubelike ultrasonic transmission/reception surface 108. Given this factor, in the embodiment 3, the end-portion of the band-like sheet member 71 is pulled in the central-axis direction of the half-cylinder part of the ultrasonic probe head 107 by adjusting the length of a pair of the band-like members 75 so as to make the constricting pressure of the end region of the longitudinal direction of the sheet membrane of the pressing unit 72 and the central region thereof to be the same.

Meanwhile, as shown in FIG. 14, both edges of the band-like sheet member 71 can be coupled by a sheet member 79 having elasticity in place of the pair of band-like members 75 shown in FIG. 11 so as to form a cap portion having the diameter which is slightly smaller than the diameter of the ultrasonic probe head 107 for spreading and covering the ultrasonic probe head 107 and to make the constricting pressure the same over the entire pressing unit 72.

Accordingly, in accordance with the embodiment 3, the pressing unit 72 can be delicately expanded/constricted in the region of the pressing unit 72 so as to generate strain in target tissues by delicate pressing operation. Also, since the threshold tensile force is applied over the entire region of the sheet membrane surface, it is possible to add the pressure which corresponds to the threshold tensile force to the contact surface region of the biological tissues without concentration of expansion/contraction on the surface region which has no contact with the target tissues, whereby facilitating a smooth pressing operation.

While the example of applying the pressing device of the present invention to the ultrasonic probe that is convex type, linear type or end-fire type for a transrectal probe in the above-described embodiments 1~3, it is also applicable to arbitrary forms of ultrasonic probes such as a transesophageal probe, endovaginal probe, finger-worn type, microscope for a blood vessel or endoscopic probe. It is characterized in applying initial tensile force to the sheet membrane of the pressing unit in the condition that a balloon is attached to an ultrasonic probe, and the form or configuration of an attachment part to apply tensile force to the sheet membrane of the pressing unit can be designed in accordance with the form of each probe. The embodiments 1~3 can be applied also to the convex type or linear type of ultrasonic probe for pressing an object from outside.

Embodiment 4

It is important to form the band-like sheet members 61 and 71 of the balloon 38 shown in the embodiments 1~3 using sufficient tensile force and constriction, and a material capable of allowing ultrasonic waves to pass through. Regarding the elasticity, the material cited in the embodiment 1 can be used. Also, in order to reduce multiple reflections of ultrasonic waves described in FIGS. 7 and 8, the material should be used which has the thinnest membrane available and matches the acoustic impedance of the biological tissues.

In place of forming the balloon 38 by the same two pieces of band-like sheets members 61a and 61b described in the embodiment 1, if the side that contacts with the target tissues 64 is, for example, the band-like sheet member 61a, the other band-like sheet member 61b does not need to have a function to expand or contract for pressing the target tissues 64. Given this factor, it is preferable to change the material, thickness and hardness of the band-like sheet member 61a and the band-like sheet member 61b, and to use the combination suitable for the purpose. For example, the sheet to use for the band-like sheet member 61b which contacts with the ultrasonic transmission/reception surface should be thinner than the band-like sheet member 61a so that the balloon 38 can have the optimal transparency for ultrasonic waves to pass through.

Embodiment 5

In the embodiments 1~4, the embodiments regarding the balloon of the pressing device related to the present invention were described. In embodiment 5, practical examples of the pressing operation unit 44 for charging/discharging liquid to/from the balloon 38 of the pressing unit related to the present invention will be described referring FIG. 15. FIG. 15 shows the conceptual composition of an embodiment of the pressing operation unit 44. As shown in FIG. 15, a tube 63 of the balloon 38 is coupled to a pressing operation syringe 82 and a bubble removing syringe 83 via a three-way cock 81. FIG. 15(1)~(5) is for illustrating the procedure to remove bubbles of the liquid charged to the balloon 38.

At the start of using the pressing device, as shown in FIG. 15(1), the liquid such as water is charged into the bubble-removing syringe 83. Then the three-way cock 81 is switched to set the condition that the balloon 38 is communicated only with the bubble-removing syringe 83. Next, as shown in FIG. 15(2), insertion/pullout of a pusher of the bubble-removing syringe 83 is repeated so as to transfer the air or air bubbles in the balloon 38 or the tube 63 (63a and 63b) to the bubble-removing syringe 83. Then as shown in FIG. 15(3), the three-way cock 81 is switched so that the bubble-removing syringe 83 is to be communicated only with the pressing operation syringe 82. Then as shown in FIG. 15(4), the liquid is charged by pulling out the pusher of the pressing operation syringe 82 and the liquid is pulled in and pushed out between the bubble-removing syringe 83 and the pressing operation syringe 82, so as to transfer the air and air bubbles in the compression operating syringe 82 to the bubble-removing syringe 83. Lastly, as shown in FIG. 15(5), the bubble-removing syringe 83 is separated off from the tube 63 by switching the three-way cock 81 so as to set the condition capable of conducting the usual pressing operation. In addition, the bubble-removing syringe 83 needs to be placed at a position higher than the balloon 38 and the compression operating syringe 82. Also, the initial charging amount V0 is adjusted by the bubble-removing syringe 83.

As described above, it is important to keep the condition of the liquid in the balloon 38 with no air bubbles. Given this factor, in accordance with the present embodiment, the bubbles can be completely removed from the liquid of the balloon 38 and the compression operating syringe 82, whereby making it possible to perform diagnosis of elastic images without any noise caused due to existence of the bubbles in the balloon 38.

Also, as described above, the balloon 38 and the tube 63 are disposed after each use. Given this factor, the balloon 38, tube 63, three-way cock 81, pressure operating syringe 82 and bubble-removing syringe 83 are combined together in advance, as a sterilized package. In this case, by charging liquid and removing the bubbles therefrom, the package can be attached to the ultrasonic probe 12 after it is opened to be used at once. Also, it is even more preferable if normal saline, degassed water, etc. is used for the liquid.

While the operation is controlled by the ultrasonic diagnostic apparatus 1 in the above embodiments, it may be set so that interface such as a button or a lever for controlling the balloon may be provided in the grip of the ultrasonic probe 12 and the examiner can switch the operation of balloon 38 with his/her hand holding the grip of the ultrasonic probe 12, or with his/her foot by a foot switch. Further, a function to recognize the commands of the examiner through his/her voice for switching operations may be provided to the apparatus.

The invention claimed is:

1. An ultrasonic probe comprising:
an end-portion having an ultrasonic transmission/reception surface;
a grip which is coupled to the end-portion, and which is for an examiner to hold with his/her hand; and
a pressing device having a balloon configured to press an object;
wherein the balloon has:
a hollow pressing unit formed by an elastic member;
a tube configured to charge/discharge liquid to/from the pressing unit;
an attachment part configured to apply the pressing unit to an ultrasonic transmission/reception surface; and
the grip has an engaging part configured to engage a hook band of the attachment part, and the hook band of the attachment part is engaged to the engaging part in extension of the pressing unit in the longitudinal direction.

2. The ultrasonic probe according to claim 1, wherein the attachment part has a cylindrical shape, and is wound on the part to which the attachment part is to be attached having the ultrasonic transmission/reception surface.

3. The ultrasonic probe according to claim 1 which comprises a pressing operation unit configured to expand/deflate the pressing unit by charging/discharging the liquid via the tube.

4. The ultrasonic probe according to claim 1, wherein the end-portion has two ultrasonic transmission/reception surfaces that are orthogonal to each other, where the pressing unit of the balloon is attached to the respective two ultrasonic transmission/reception surfaces.

5. An ultrasonic diagnostic apparatus comprising:
the ultrasonic probe provided according to any of claims 1, 2, 3 or 4;
a processor configured to control adding pressure to biological tissues of an object to be examined via the ultrasonic probe, obtain elasticity information of the biological tissues in a plurality of measuring points based on a pair of frame data acquired by measuring reflected echo signals generated from the object, and construct an elastic image based on the obtained elasticity information; and
a display configured to display the elastic image.

6. The ultrasonic diagnostic apparatus according to claim 5, comprising a pressure sensor configured to measure the pressure in the pressing unit.

7. An ultrasonic probe comprising:
an end-portion having an ultrasonic transmission/reception surface;
a grip which is coupled to the end-portion, and which is for an examiner to hold with his/her hand; and
a pressing device having a balloon configured to press an object;
wherein the balloon has:
a hollow pressing unit formed by an elastic member;
a tube configured to charge/discharge liquid to/from the pressing unit;
an attachment part configured to apply the pressing unit to an ultrasonic transmission/reception surface;
the grip has an engaging part configured to engage a hook band of the attachment part, and the hook band of the attachment part is engaged to the engaging part in the longitudinal direction;
where the end-portion is adjustably extendable relative to the grip, in the longitudinal direction of the ultrasonic probe; and
wherein extendable adjustment of the end-portion to extend further from the grip, with the hook band engaged to the engaging part of the grip, effects an increased constriction force of the pressing unit on the end-portion, and extendable adjustment of the end-portion to extend closer to the grip, effects a decreased constriction force of the pressing unit on the end-portion.

* * * * *